US011135346B2

(12) United States Patent
Hobro et al.

(10) Patent No.: US 11,135,346 B2
(45) Date of Patent: *Oct. 5, 2021

(54) DIALYSIS MACHINE, METHOD OF CONTROLLING THE DIALYSIS MACHINE, AND COMPUTER PROGRAM FOR IMPLEMENTING THE CONTROL

(71) Applicant: GAMBRO LUNDIA AB, Lund (SE)

(72) Inventors: Sture Hobro, Lund (SE); Olof Jansson, Vellinge (SE); Jan Lunsjo, Eslov (SE)

(73) Assignee: Gambro Lundia AB, Lund (SE)

( * ) Notice: Subject to any disclaimer, the term of this patent is extended or adjusted under 35 U.S.C. 154(b) by 378 days.

This patent is subject to a terminal disclaimer.

(21) Appl. No.: 16/124,454

(22) Filed: Sep. 7, 2018

(65) Prior Publication Data

US 2019/0001040 A1    Jan. 3, 2019

Related U.S. Application Data

(63) Continuation of application No. 15/108,907, filed as application No. PCT/EP2014/078401 on Dec. 18, 2014, now Pat. No. 10,092,686.

(30) Foreign Application Priority Data

Dec. 30, 2013 (SE) .................................. 1351590-3

(51) Int. Cl.
*A61M 1/16* (2006.01)
*A61L 2/18* (2006.01)
(Continued)

(52) U.S. Cl.
CPC .............. *A61M 1/169* (2013.01); *A61L 2/18* (2013.01); *A61L 2/24* (2013.01); *A61M 1/168* (2013.01);
(Continued)

(58) Field of Classification Search
CPC .... A61M 1/169; A61M 1/168; A61M 1/1682; A61L 2/18
See application file for complete search history.

(56) References Cited

U.S. PATENT DOCUMENTS

| 3,809,241 A | 5/1974 | Alvine |
| 4,018,684 A | 4/1977 | Uffer |

(Continued)

FOREIGN PATENT DOCUMENTS

| CN | 202961313 | 6/2013 |
| DE | 2934167 | 3/1981 |

(Continued)

OTHER PUBLICATIONS

International Search Report PCT/EP2014/078401—dated Apr. 1, 2015—5 pages.

(Continued)

*Primary Examiner* — Kevin Joyner
(74) *Attorney, Agent, or Firm* — K&L Gates LLP

(57) ABSTRACT

In an embodiment, a dialysis machine includes a dialyser, a fluid line in fluid communication with the dialyser, an inlet valve enabling fluid to flow into the fluid line towards the dialyser during a dialysis treatment, a disinfectant line connected to the fluid line via a disinfectant valve upstream of the dialyser, the disinfectant valve enabling a disinfectant fluid to be provided to at least part of the fluid line during a disinfection procedure, and a controller programmed to open the inlet valve, while the disinfectant line is connected to a source of disinfectant fluid, to create a positive pressure gradient across the disinfectant valve as fluid flows into the fluid line towards the dialyser, the positive pressure gradient ensuring that the disinfectant fluid from the source of disinfectant fluid does not leak into the fluid line during the dialysis treatment.

23 Claims, 12 Drawing Sheets

(51) Int. Cl.
*A61L 2/24* (2006.01)
*A61M 39/22* (2006.01)

(52) U.S. Cl.
CPC ........ *A61M 1/1682* (2014.02); *A61M 39/223* (2013.01); *A61L 2202/14* (2013.01); *A61L 2202/24* (2013.01); *A61M 1/1688* (2014.02); *A61M 2205/15* (2013.01); *A61M 2205/3331* (2013.01); *A61M 2205/36* (2013.01); *A61M 2205/702* (2013.01)

(56) References Cited

U.S. PATENT DOCUMENTS

| | | | |
|---|---|---|---|
| 4,153,554 | A | 5/1979 | von der Heide et al. |
| 4,683,053 | A | 7/1987 | Polaschegg |
| 4,789,467 | A | 12/1988 | Lindsay et al. |
| 5,591,344 | A | 1/1997 | Kenley et al. |
| 5,895,578 | A | 4/1999 | Simard et al. |
| 6,051,188 | A | 4/2000 | Spickermann et al. |
| 6,579,494 | B1 | 6/2003 | Chevallet et al. |
| 2004/0079700 | A1 | 4/2004 | Wood et al. |
| 2004/0215129 | A1 | 10/2004 | Edgson et al. |
| 2005/0171501 | A1 | 8/2005 | Kelly |
| 2006/0291839 | A1 | 12/2006 | Yano |
| 2007/0102357 | A1 | 5/2007 | Weatherill |
| 2009/0113335 | A1 | 4/2009 | Sandoe et al. |
| 2009/0134080 | A1 | 5/2009 | Fabig |
| 2009/0206017 | A1 | 8/2009 | Rohde et al. |
| 2011/0192796 | A1 | 8/2011 | Smejtek et al. |
| 2012/0308431 | A1 | 12/2012 | Kotsos et al. |
| 2013/0264250 | A1 | 10/2013 | Brugger et al. |
| 2014/0098627 | A1 | 4/2014 | Mochizuki et al. |

FOREIGN PATENT DOCUMENTS

| | | |
|---|---|---|
| DE | 3416955 | 11/1985 |
| DE | 3447989 | 1/1986 |
| DE | 10013964 | 9/2001 |
| DE | 10310418 | 9/2004 |
| DE | 19655227 | 8/2009 |
| EP | 0428009 | 5/1991 |
| EP | 1236685 | 9/2002 |
| EP | 2719406 | 4/2014 |
| JP | 2004049977 | 2/2004 |
| JP | 2009056271 | 3/2009 |
| JP | 2010194092 | 9/2010 |
| WO | 9609080 | 3/1996 |
| WO | 9625214 | 8/1996 |
| WO | 96/40313 | 12/1996 |
| WO | 0057928 | 10/2000 |
| WO | 0057935 | 10/2000 |
| WO | 2012119799 | 9/2012 |
| WO | 2012/169527 | 12/2012 |

OTHER PUBLICATIONS

Written Opinion of the International Searching Authority PCT/EP2014/078401—dated Apr. 1, 2015—8 pages.
Search Report for International Patent Application PCT/EP2014/074236 dated Jan. 21, 2015 (4 pages).
Written Opinion for International Patent Application PCT/EP2014/074236 dated Jan. 21, 2015 (6 pages).
International Search Report and Written Opinion dated Feb. 4, 2014, for related International Appln. No. PCT/EP2013/073705 (12 pages).
Rosenberg, "Thermal Disinfection—The A0 Concept and the Biological Background", Central Sterilisation, 2003, vol. 11, pp. 118-120.
English translation of Office Action issued in corresponding Chinese Patent Application No. 201410709722.4 dated Aug. 18, 2017.

DIALYSIS MACHINE, METHOD OF CONTROLLING THE DIALYSIS MACHINE, AND COMPUTER PROGRAM FOR IMPLEMENTING THE CONTROL

PRIORITY CLAIM

The present application is a continuation of U.S. application Ser. No. 15/108,907, entitled, "Dialysis Machine, Method of Controlling the Dialysis Machine, and Computer Program for Implementing the Control", filed Jun. 29, 2016, which is a National Phase of International Application No. PCT/EP2014/078401, filed Dec. 18, 2014, which claims priority to Swedish Patent Application No. 1351590-3, filed Dec. 30, 2013, the entire contents of each of which are incorporated herein by reference and relied upon.

TECHNICAL FIELD

The present invention generally relates to a dialysis machine, a method of controlling the dialysis machine, and a computer program for implementing the control. In particular, the present invention relates to providing disinfectant for disinfection of the dialysis machine.

BACKGROUND

Dialysis machines are routinely rinsed after each use an commonly are disinfected at the end of the day. Disinfection may be using heat or bleach, and is often preceded by a vinegar rinse to remove carbonate encrustations and build-up in the tubing passages. Different used substances used at disinfection are hereafter discussed using the general term "disinfectant".

During treatment using a dialysis machine, it is important that disinfectant does not reach the patient, and thus not the dialysis fluid during treatment. A valve for letting disinfectant into a fluid circuit of the dialysis machine prevents this. However, as with all components, the valve may malfunction and provide some leakage. Thus, a valve only cannot be relied on. Therefore, it is conventional that a disinfectant source is disconnected before treatment commences, and that the disinfectant intake connector is normally put in a connector parking position such that the dialysis machine by sensors, which senses the presence of the disinfectant intake connector in the parking position, can ascertain that the operator has disconnected the disinfectant source. The solution is of course safeguarding that no disinfectant can reach the fluid circuit during treatment, but, the operator is given additional manual tasks which is time consuming for the operator and thus less efficient in sense of labour resources. It is therefore desired to provide a solution which decreases manual tasks for the operator, but still safeguards that no disinfectant can reach the fluid circuit during treatment.

SUMMARY OF THE INVENTION

An object of the invention is to at least alleviate the above stated problem. The present invention is based on the understanding that a valve connected between a disinfectant source and the fluid circuit, although a malfunction of the valve giving some leakage occurs, will not provide any disinfectant to the fluid circuit if connected at a position in the fluid circuit where a pressure gradient is present during treatment taking any leaking disinfectant away from the rest of the fluid circuit. Instead, such leakage will be in the other direction, i.e. either the disinfectant may be more or less diluted by water, which causes significantly less harm since dilution of disinfectant may be detected and the issue of leakage fixed or the disinfectant leak is provided out from the circuit, e.g. via a pipe ending in free air, and no patient is exposed to the disinfectant. "Treatment" should here be construed generously, e.g. including parts of setup before a patient is connected, such as priming, etc., where a patient may be exposed later to substances introduced in the fluid circuit. The inventors have also found that this pressure gradient is provided between a positive pressure, e.g. provided by a pure water inlet of the dialysis machine and/or downstream pumps of the dialysis machine, and a lower pressure present in the disinfectant source and/or pipe(s) ending in free air. Thereby, the disinfectant source need not be disconnected by an operator from the dialysis machine during treatment, whereby labour load may be decreased.

According to a first aspect, there is provided a dialysis machine comprising a fluid circuit for providing a dialysis fluid to a dialyser, wherein the fluid circuit comprises a tube with a first valve for providing a disinfectant fluid for disinfecting at least a part of the fluid circuit at disinfection of the dialysis machine, characterised in that the tube with the first valve is arranged to provide the disinfectant fluid upstream the dialyser and at a position in the fluid circuit where pressure is, during treatment, such that a pressure gradient between ports of the first valve is provided, the ports comprising at least a disinfectant fluid port and a fluid circuit port, such that the disinfectant fluid port of the first valve is enabled to be safely connected to a source of disinfectant also during treatment.

The position for inserting the disinfectant may be downstream a pump for concentrate distribution. The first valve may be a three-way valve with a first connection towards the source of disinfectant, a second connection towards the pump for concentrate distribution, and a third connection towards the fluid circuit leading to the dialyser, and the first valve may be arranged to either connect the first and second connections, or the second and third connections for fluid flow.

The first valve may be a three-way valve with a first connection towards the source of disinfectant, a second connection towards the fluid circuit, and a third connection towards atmospheric pressure surroundings, and the first valve is arranged to either connect the first and second connections, or the first and third connections for fluid flow.

The fluid circuit may comprise an inlet for pure water, and the position for inserting the disinfectant may be downstream the inlet such that the pressure is always positive during treatment due to pressure of the pure water. The dialysis machine may further comprise a second valve arranged upstream a point of the fluid circuit where the pure water is arranged to mix with distributed concentrate such that, when the second valve is closed during at least a part of the disinfection operation, a pump for concentrate distribution may be enabled to suck up the disinfectant and distribute the disinfectant into the fluid circuit. The second valve may be a one-way valve.

The dialysis machine may further comprise a bypass coupling arranged to receive dialyser fluid connection lines such that, at disinfection operation, the bypass coupling is employed to connect the dialysis machine upstream dialyser fluid path with the dialysis machine downstream dialyser fluid path and to establish a connection to a pure water inlet. The first valve may be a three-way valve with a first connection towards the source of disinfectant, a second connection towards a tube in connection with the pure water inlet, and a third connection towards the bypass coupling, and the valve may be arranged to either connect the first and second connections, or the second and third connections for fluid flow. The dialysis machine may further comprise a third valve being a three-way valve with a first connection towards the second connection of the first valve, a second connection towards a tube in connection with the pure water inlet, and a third connection towards a concentrate connector of the machine, and the third valve may be arranged to either connect the second and third connections, or the first and third connections for fluid flow.

The dialysis machine may comprise a disinfectant selection valve arranged to enable selection of one of several disinfectant sources as the source of disinfectant.

According to a second aspect, there is provided a method of controlling a fluid circuit for providing a dialysis fluid to a dialyser and disinfection operation of a dialysis machine according to the first aspect. The method comprises controlling the first valve to prevent connection of the disinfectant source to the fluid circuit during treatment; and controlling the first valve to connect the disinfectant source to the fluid circuit during disinfection operation.

The position for inserting the disinfectant may be downstream a pump for concentrate distribution and the first valve is a three-way valve with a first connection towards the source of disinfectant, a second connection towards the pump for concentrate distribution, and a third connection towards the fluid circuit leading to the dialyser, and the first valve may be arranged to either connect the first and second connections in a first state, or the second and third connections for fluid flow in a second state, wherein the method may comprise controlling the first valve to be in the first state and controlling the pump for concentrate distribution to provide fluid flow in a first direction during disinfection operation; and controlling the first valve to be in the second state and controlling the pump for concentrate distribution to provide fluid flow in a second direction opposite to the first direction during treatment.

The fluid circuit may comprise a bypass coupling arranged to receive dialyser fluid connection lines such that, at disinfection operation, the bypass coupling is employed to connect the dialysis machine upstream dialyser fluid path with the dialysis machine downstream dialyser fluid path and to establish a connection to a pure water inlet, the first valve may be a three-way valve with a first connection towards the source of disinfectant, a second connection towards a tube in connection with the pure water inlet, and a third connection towards the bypass coupling, wherein the method may comprise connecting at treatment the dialysis machine upstream dialyser fluid path and the dialysis machine downstream dialyser fluid path, respectively, with the dialyser, and controlling the valve to connect the second and third connections for fluid flow; and at disinfection operation, connecting the dialysis machine upstream dialyser fluid path and the dialysis machine downstream dialyser fluid path to the bypass coupling, and controlling the valve to connect the first and second connections for fluid flow. The fluid circuit may further comprise a third valve being a three-way valve with a first connection towards the second connection of the first valve, a second connection towards a tube in connection with the pure water inlet, and a third connection towards a concentrate connector of the machine, wherein the method may comprise, at treatment, controlling the third valve to connect the second and third connections for fluid flow; and, at disinfection operation, controlling the third valve to connect the first and third connections for fluid flow.

The dialysis machine may comprise a disinfection fluid tank arranged to intermediately store disinfection fluid and the disinfection fluid tank is connected to the second connection of the first valve. The dialysis machine may also comprise a coupling arrangement comprising a dialyser downstream connector and a dialyser upstream connector, and the coupling arrangement is arranged to receive dialyser fluid connection lines such that, at disinfection operation, the coupling arrangement is employed to connect the dialysis machine upstream dialyser fluid path with the disinfection fluid tank to establish a connection to a pure water inlet, and the dialysis machine downstream dialyser fluid path to a drain line of the dialysis machine via a fourth valve, wherein a first path and a second path are formed at disinfection, wherein the first path comprises a loop of the disinfection fluid tank via the first valve and a path from the pure water inlet line to the dialyser upstream connector to the disinfection fluid tank, and the second path comprises a loop of the dialyser downstream connector and a drainage pump via the fourth valve to the dialyser downstream connector, and when not performing disinfection, the first and fourth valves are closed. The dialysis machine may comprise a bypass valve, wherein the bypass valve is arranged to provide disinfectant from the first path to the second path.

A disinfectant selection valve may be arranged to enable selection of one of several disinfectants as the source of disinfectant, wherein the method may comprise controlling the disinfectant selection valve at disinfection operation according to a predetermined disinfection scheme.

According to a third aspect, there is provided a computer program, for a controller of a dialysis machine, comprising computer program code including computer executable instructions, which when downloaded and executed by a processor of the controller causes the controller to control the dialysis machine to perform the method according to the second aspect.

Other objectives, features and advantages of the present invention will appear from the following detailed disclosure, from the attached dependent claims as well as from the drawings. Generally, all terms used in the claims are to be interpreted according to their ordinary meaning in the technical field, unless explicitly defined otherwise herein. All references to "a/an/the [element, device, component, means, step, etc]" are to be interpreted openly as referring to at least one instance of said element, device, component, means, step, etc., unless explicitly stated otherwise. The steps of any method disclosed herein do not have to be performed in the exact order disclosed, unless explicitly stated.

BRIEF DESCRIPTION OF THE DRAWINGS

The above, as well as additional objects, features and advantages of the present invention, will be better understood through the following illustrative and non-limiting detailed description of preferred embodiments of the present invention, with reference to the appended drawings.

DETAILED DESCRIPTION

Figure 1:
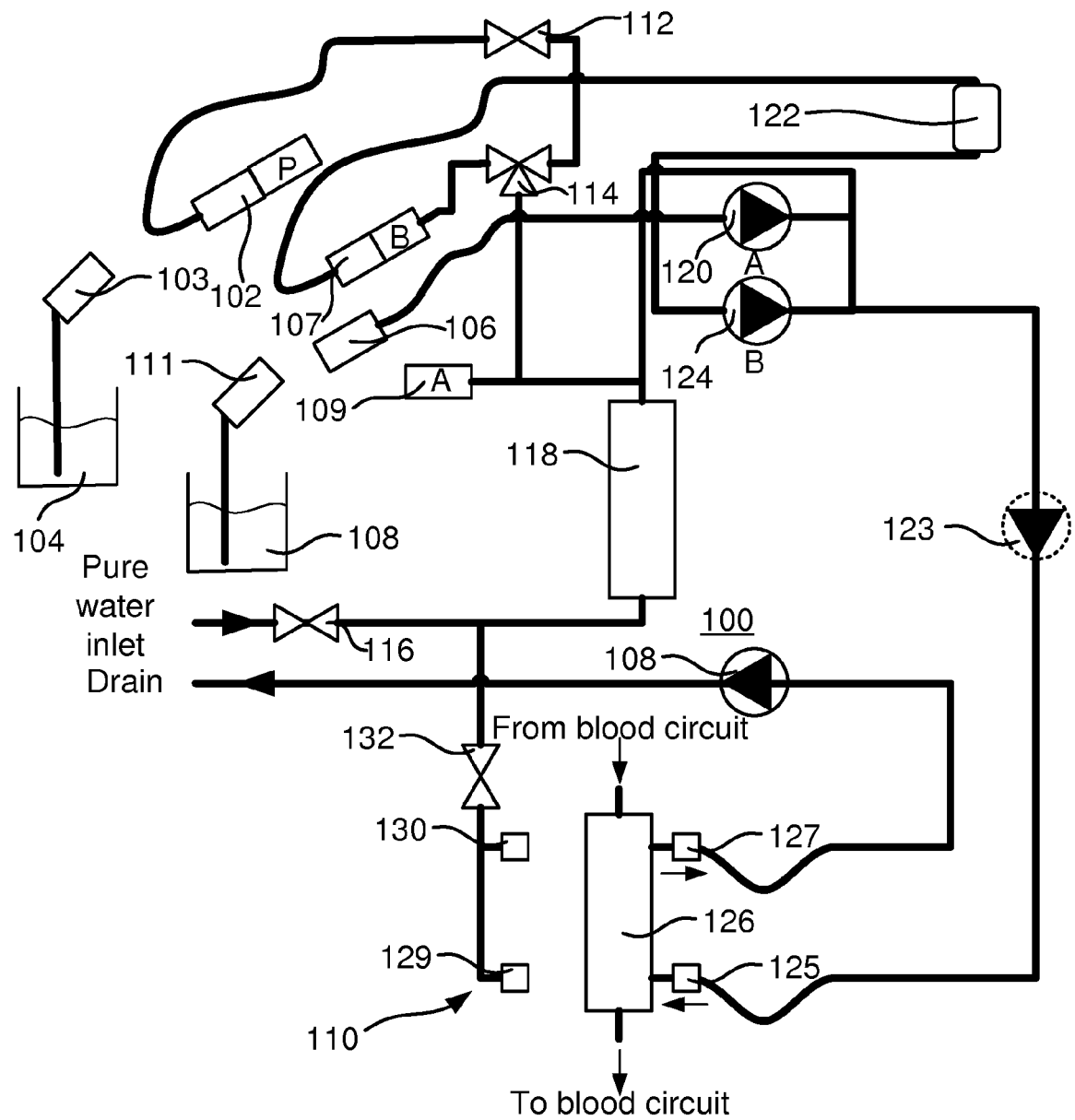
FIG. 1 schematically illustrates a dialysis machine with conventional connector arrangement for disinfectant.

The aim is to provide a solution which decreases manual tasks for the operator, but still safeguards that no disinfectant can reach the fluid circuit during treatment. A valve for letting disinfectant into a fluid circuit of the dialysis machine prevents this. However, as with all components, the valve may malfunction and provide some leakage. Thus, a valve only cannot be relied on. Therefore, as illustrated in FIG. 1, it is conventional that a disinfectant source is disconnected before treatment commences, and that the connector is normally put in a connector parking position such that the dialysis machine by sensors, which senses the presence of the connector in the parking position, can ascertain that the operator has disconnected the disinfectant source. The solution is of course safeguarding that no disinfectant can reach the fluid circuit during treatment, but, the operator is given additional manual tasks which can be considered less efficient in sense of labour resources. It is therefore desired to provide a solution which decreases manual tasks for the operator, but still safeguards that no disinfectant can reach the fluid circuit during treatment.

Figure 11:
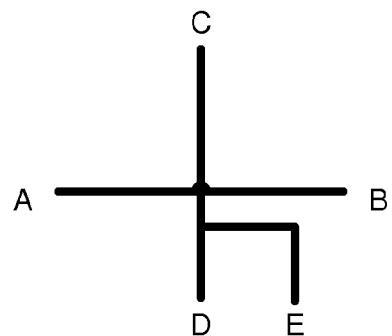
FIG. 11 is a fluid scheme for explaining connections etc. of FIGS. 1 to 10.

FIG. 1 schematically illustrates a dialysis machine 100 with conventional connector arrangement for disinfectant. It is to be noted that elements, commonly present in a dialysis machine, but which are not of particular relevance for understanding the gist of this disclosure, are not depicted in detail. In the drawings, numerous of tubes interconnect different elements. For the understanding of the schematic illustrations, FIG. 11 is first to be considered. FIG. 11 illustrates two crossing tubes which are not interconnected, which is illustrated by the "jump" at the position where they cross. Further, one of the tubes is branched. Thus A is connected with B, but there is no connection between A or B to any of C, D or E. C and D are connected, and are also connected to E. The illustrations should be readily understood from this.

A disinfectant connector 102 is arranged to either be connected to a connector 103 for drawing disinfectant from a disinfectant source 104, or be connected to a parking position connector P for ensuring that the disinfectant source 104 is disconnected from a fluid circuit of the dialysis machine 100. In FIG. 1, the disinfectant connector 102 is in its parking position P. The disinfectant connector 102 is connected via a disinfectant valve 112 to the fluid circuit of the dialysis machine 100.

The dialysis machine 100 comprises a pure water inlet which via a water valve 116 and a water heater 118 provides water for preparing desired fluids in the fluid circuit. The output of the water heater 118 is provided to a connector A 109, to a three-way valve 114, which is also connected to the disinfectant valve 112 and to a connector B 107, and to a position downstream a first concentrate pump A 120. The first concentrate pump A 120 is upstream connected to a connector 106 which is arranged to either be connected to the connector A 109, or to a concentrate A connector 111 providing concentrate A from a concentrate source 108.

The connector B may be connected to a connector 107 which in turn is connected via a tube towards a dry concentrate cartridge holder 122 and the output of the dry concentrate holder is provided to a concentrate pump B 124. The concentrate pump B 124 is thus able to draw concentrate from the dry concentrate holder which is provided pure water via the three-way valve 114.

Concentrate output from concentrate pump A 120 is mixed with pure water downstream the concentrate pump A 120, and the mix therefrom is further downstream mixed with output from concentrate pump B 124. The mix forms the dialysis fluid and is, for example by a flow pump 123 or by the pure water pressure, provided to a first connection 125 of a dialyser 126. Another flow pump 128 pumps the spent dialysis fluid from the dialyzer 126 through the second connection 127 towards the drain. The flow pumps 123 and 128 may be controlled such that an appropriate amount of water is removed from the patient during treatment.

During disinfection, the disinfection valve 112 and three-way valve 114 are set in position for letting disinfectant reach the fluid circuit of the dialysis machine. The disinfection connector 102 is also moved from the parking connector P to the connector 103 of the disinfectant source 104. Here, it is to be noted that during disinfection operation, the connector 106 is moved from connector 111 to a connector A 109, whereby it can be seen that the corresponding concentrate pump A 120 can draw disinfectant through the fluid circuit. It can also be noted that fluid connection lines, which at treatment are connected to the dialyser 126, may at disinfection be disconnected from connectors 125, 127 of the dialyser 126 and be connected to a bypass connection 110, i.e. to connectors 129, 130 of the bypass connection 110, which is employed to connect the dialysis machine upstream dialyser fluid path with the dialysis machine downstream dialyser fluid path. The bypass connection is also, via a valve 132, connected to a water line between the water valve 116 and the heater 118 to establish a connection to the pure water inlet. This enables disinfection of all parts of the fluid circuit.

FIGS. 2 to 6 schematically illustrate a dialysis machine with an arrangement for disinfectant according to embodiments, respectively. The elements of the dialysis machine which does not have a direct impact on the contribution of providing a solution which decreases manual tasks for the operator, but still safeguards that no disinfectant can reach the fluid circuit during treatment are shown as examples in FIGS. 2 to 6, but other designs of the dialysis machine are equally feasible for the principles of this disclosure, as will be readily understood from the description below. Further, these elements are not described further unless they have any impact on particular embodiments for the providing of a solution which decreases manual tasks for the operator, which still safeguards that no disinfectant can reach the fluid circuit during treatment.

Figure 2:
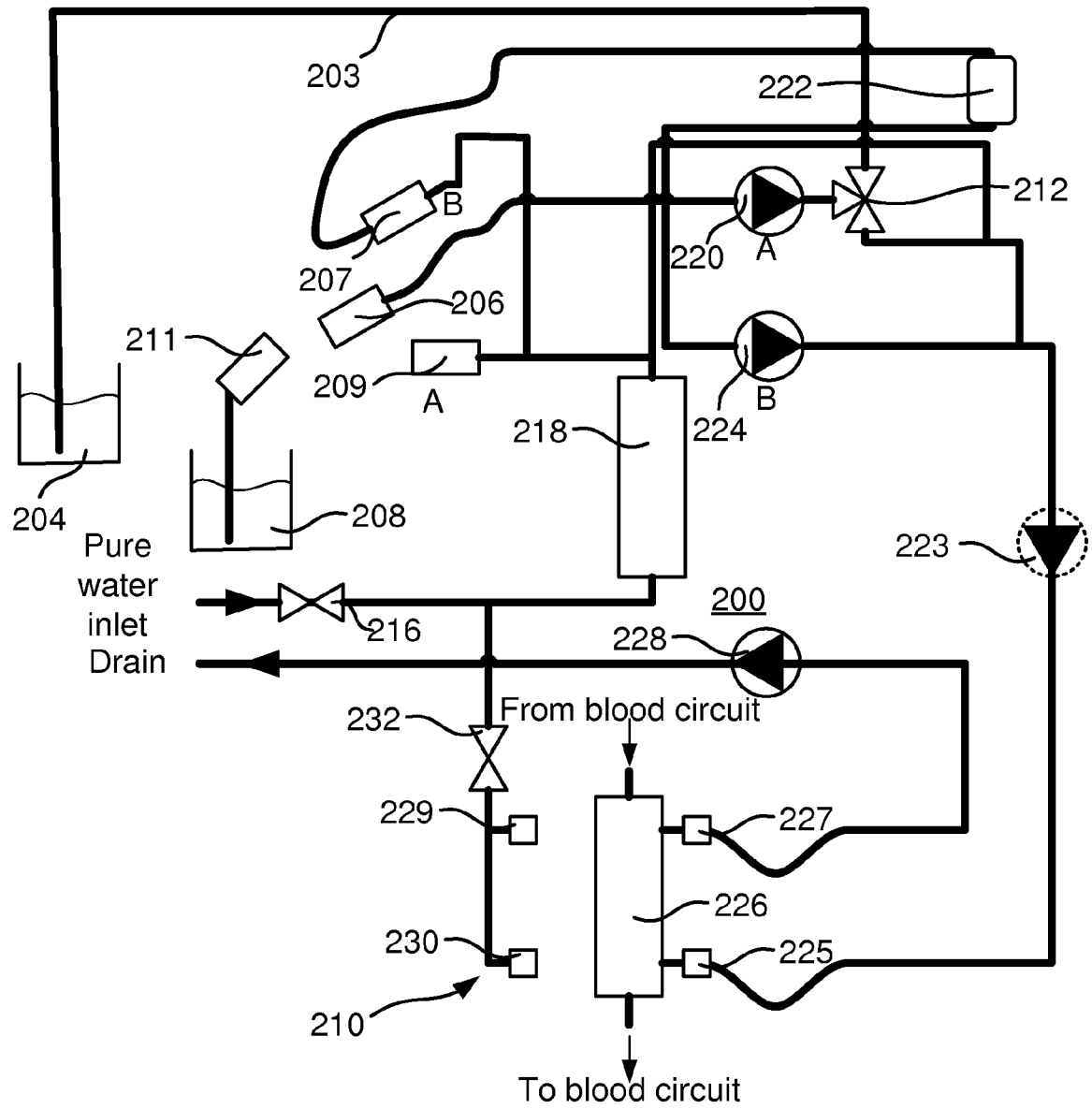
FIGS. 2 to 9 schematically illustrate a dialysis machine with an arrangement for disinfectant according to embodiments, respectively.

The dialysis machine 200 of FIG. 2 provides a disinfectant source 204 which is connected by a tube 203 for drawing disinfectant from a disinfectant source 204. For ensuring that the disinfectant source 204 does not provide any disinfectant to a fluid circuit of the dialysis machine 200 when a patient is connected, the tube 203 is connected with a first valve 212 for providing the disinfectant fluid for disinfecting at least a part of the fluid circuit at disinfection of the dialysis machine, wherein the tube 203 with the first valve 212 is arranged to provide the disinfectant fluid upstream a dialyser 226 and at a position in the fluid circuit where pressure is, during treatment, such that a pressure gradient between disinfectant fluid port and fluid circuit port of the first valve 212 is provided away from the fluid circuit.

The dialysis machine 200 comprises a pure water inlet which via a water valve 216 and a water heater 218 provides water for preparing desired fluids in the fluid circuit. The output of the water heater 218 is provided to a connector A 209 and to a connector B 207, and to the first valve 212 at a position downstream a first concentrate pump A 220. The first concentrate pump A 220 is upstream connected to a connector 206 which is arranged to either be connected to the connector A 209, or to a concentrate A connector 211 providing concentrate A from a concentrate source 208.

The connector B may be connected to a connector 207 which in turn is connected via a tube towards a dry concentrate cartridge holder 222 and the output of the dry concentrate holder is provided to a concentrate pump B 224. The concentrate pump B 224 is thus able to draw concentrate from the dry concentrate holder which is provided pure water via the connector B 207.

Concentrate output from concentrate pump A 220 is mixed with pure water downstream the concentrate pump A 220 and the first valve 212, and the mix therefrom is further downstream mixed with output from concentrate pump B 224. The mix forms the dialysis fluid and is provided to a first connection 225 of a dialyser 226 wherein the fluid may be provided to the dialyzer 226 by a pump 223 and is drawn through the dialyser 226 by a flow pump 228 and exits the dialyser 226 through a second connection 227 thereof. The flow pumps 223 and 228 may be controlled such that an appropriate amount of water is removed from the patient during treatment. The dialysate, i.e. the spent dialysis fluid, is provided towards a drain by the flow pump 228.

During disinfection, the disinfection valve 212 is set in position for letting disinfectant reach the fluid circuit of the dialysis machine. Disinfectant may be drawn through the fluid circuit by flow pump 223. Here, it is to be noted that during disinfection operation, the connector 206 may be moved to the connector A 209, whereby it can be seen that the corresponding concentrate pump A 220 can draw disinfectant through parts of the fluid circuit. It can also be noted that fluid connection lines, which at treatment are connected to the dialyser 226, may at disinfection be disconnected from connectors 225, 227 of the dialyser 226 and be connected to a bypass connection 210, i.e. to connectors 229, 230 of the bypass connection 210, which is employed to connect the dialysis machine upstream dialyser fluid path with the dialysis machine downstream dialyser fluid path. The bypass connection is also, via a valve 232, connected to a water line between the water valve 216 and the heater 218 to establish a connection to the pure water inlet. This enables disinfection of all parts of the fluid circuit.

The first valve is arranged to provide the disinfectant fluid upstream a dialyser 226 and at a position in the fluid circuit where pressure is positive during treatment such that an inlet of the first valve is enabled to be safely connected to the disinfectant source 204 also during treatment without any disinfectant being able to reach the fluid circuit when a patient is connected. The position downstream the pump 220 for concentrate distribution A provides a positive pressure from the water which the concentrate is to be mixed with, and also due to the pump operation. The first valve 212 may be a three-way valve with a first connection towards the disinfectant source 204 via the tube 203, a second connection towards the pump 220 for concentrate distribution A, and a third connection towards the fluid circuit leading to the dialyser 226. The three-way valve 212 may be arranged to connect the first and second connections, i.e. the disinfectant to the A pump, wherein the A pump may be driven to suck the disinfectant and provide it through the connector A 206, which may be connected to connector 207, and thereby further through the fluid circuit during disinfection. The three-way valve 212 may also be arranged to connect the second and third connections for fluid flow, i.e. the pump 220 to the part of the fluid circuit which is downstream during treatment. Thus, during treatment, the pump 220 is driven in opposite direction to how it is driven during disinfection, whereby it inherently provides a positive pressure at the position of the first valve 212 which in addition to the water pressure ensures the effect. Thus, any leakage in the valve 212 provides a flow from the valve 212 towards the tube 203, and it is safeguarded that no disinfectant will reach the fluid circuit during treatment if the valve 212 is malfunctioning.

Figure 3:
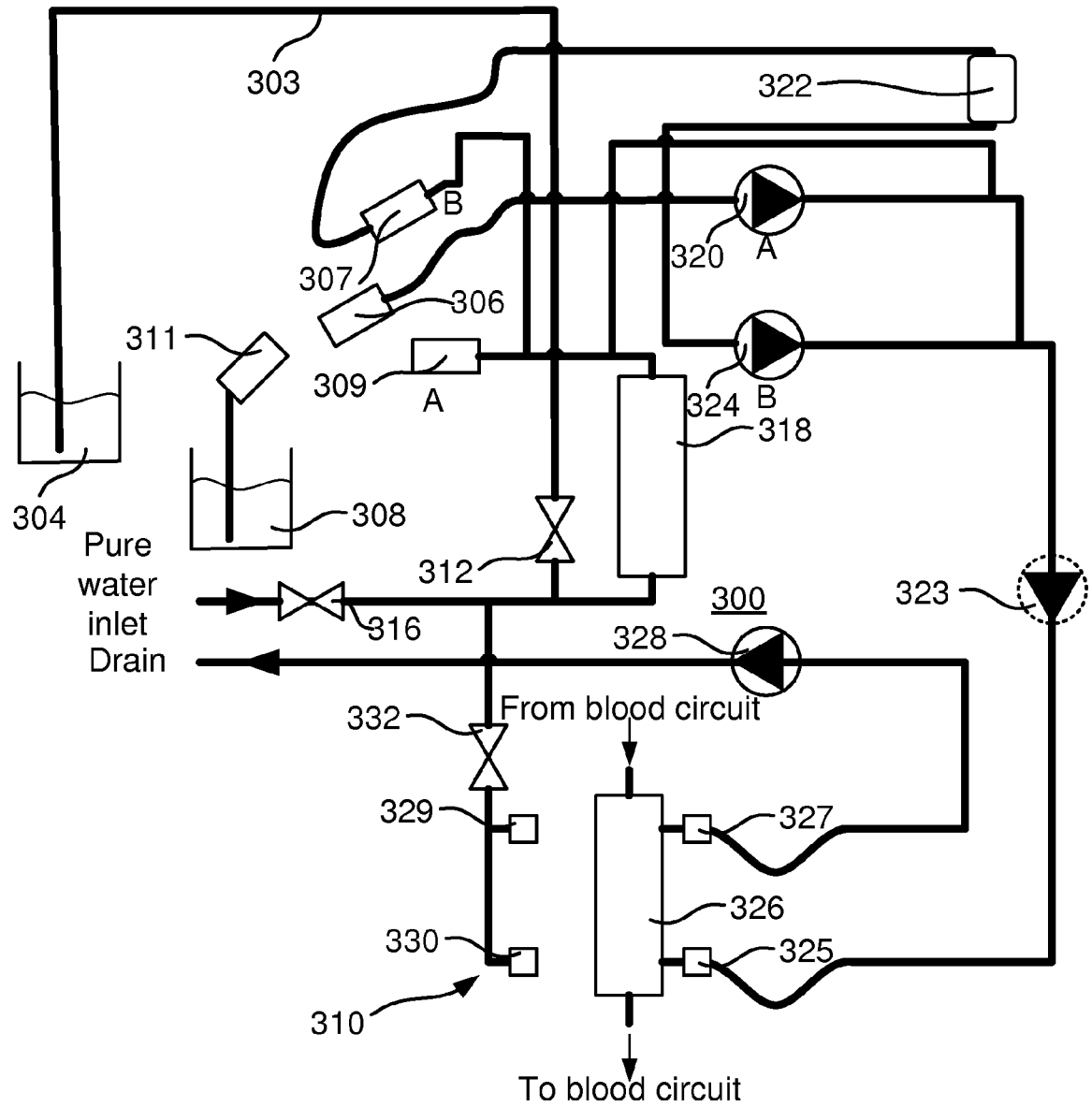

FIG. 3 illustrates a dialysis machine 300 similar to the ones depicted in FIGS. 1 and 2, but with an alternative embodiment of the position of inserting the disinfectant. It is inherent that the water inlet provides a positive pressure, wherein the position provides similar properties as the embodiment of FIG. 2. Thus, any leakage due to malfunctioning valve 312 only causes dilution of the disinfectant by water which may leak towards a disinfectant source 304.

The dialysis machine 300 of FIG. 3 provides a disinfectant source 304 which is connected by a tube 303 for drawing disinfectant from a disinfectant source 304. For similar reasons as demonstrated with reference to FIG. 2, the tube 303 is connected with a first valve 312 for providing the disinfectant fluid upstream a dialyser 326 and at a position in the fluid circuit where pressure is, during treatment, such that a pressure gradient between disinfectant fluid port and fluid circuit port of the first valve 312 is provided away from the fluid circuit. The dialysis machine 300 comprises a pure water inlet which via a water valve 316 and a water heater 318 provides water for preparing desired fluids in the fluid circuit. The fluid circuit port of the first valve 312 is connected to the tube connection between the water valve 316 and the water heater 318. The water pressure by the pure water will thus provide the pressure gradient. The output of the water heater 318 is provided to a connector A 309 and to a connector B 307, and to a position downstream a first concentrate pump A 320. The first concentrate pump A 320 is upstream connected to a connector 306 which is arranged to either be connected to the connector A 309, or to a concentrate A connector 311 providing concentrate A from a concentrate source 308.

The connector B 307 may be connected via a tube towards a dry concentrate cartridge holder 322 and the output of the dry concentrate holder is provided to a concentrate pump B 324. The concentrate pump B 324 is thus able to draw concentrate from the dry concentrate holder which is provided pure water via the connector B 307.

Concentrate output from concentrate pump A 320 is mixed with pure water downstream the concentrate pump A 320, and the mix therefrom is further downstream mixed with output from concentrate pump B 324. The mix forms the dialysis fluid and is provided to a first connection 325 of a dialyser 326 wherein the fluid may be provided to the dialyzer 326 by a pump 323 and is drawn through the dialyser 326 by a flow pump 328 and exits the dialyser 326 through a second connection 327 thereof. The flow pumps 323 and 328 may be controlled such that an appropriate amount of water is removed from the patient during treatment. The dialysate, i.e. the spent dialysis fluid, is provided towards a drain by the flow pump 328.

During disinfection, the disinfection valve 312 is set in position for letting disinfectant reach the fluid circuit of the dialysis machine. Disinfectant may be drawn through the fluid circuit by flow pump 323. Here, it is to be noted that during disinfection operation, the connector 306 may be moved to the connector A 309, whereby it can be seen that the corresponding concentrate pump A 320 can draw disinfectant through parts of the fluid circuit. It can also be noted that fluid connection lines, which at treatment are connected to the dialyser 326, may at disinfection be disconnected from connectors 325, 327 of the dialyser 326 and be connected to a bypass connection 310, i.e. to connectors 329, 330 of the bypass connection 310, which is employed to connect the dialysis machine upstream dialyser fluid path with the dialysis machine downstream dialyser fluid path. The bypass connection is also, via a valve 332, connected to a water line between the water valve 316 and the heater 318 to establish a connection to the pure water inlet. This enables disinfection of all parts of the fluid circuit. A further advantage with the above demonstrated position for inserting the disinfectant is that it enables using the heater for heating the disinfectant for cases where the disinfectant is more efficient at higher temperatures.

The first valve is arranged to provide the disinfectant fluid upstream the dialyser 326 and at a position in the fluid circuit where pressure is positive during treatment such that an inlet of the first valve is enabled to be safely connected to the disinfectant source 304 also during treatment without any disinfectant being able to reach the fluid circuit when a patient is connected. The pure water inlet provides a water pressure during treatment that is higher than the pressure provided from the tube 303. Thus, any leakage in the valve 312 provides a flow from the valve 312 towards the tube 303, and it is safeguarded that no disinfectant will reach the fluid circuit during treatment if the valve 312 is malfunctioning.

Figure 4:
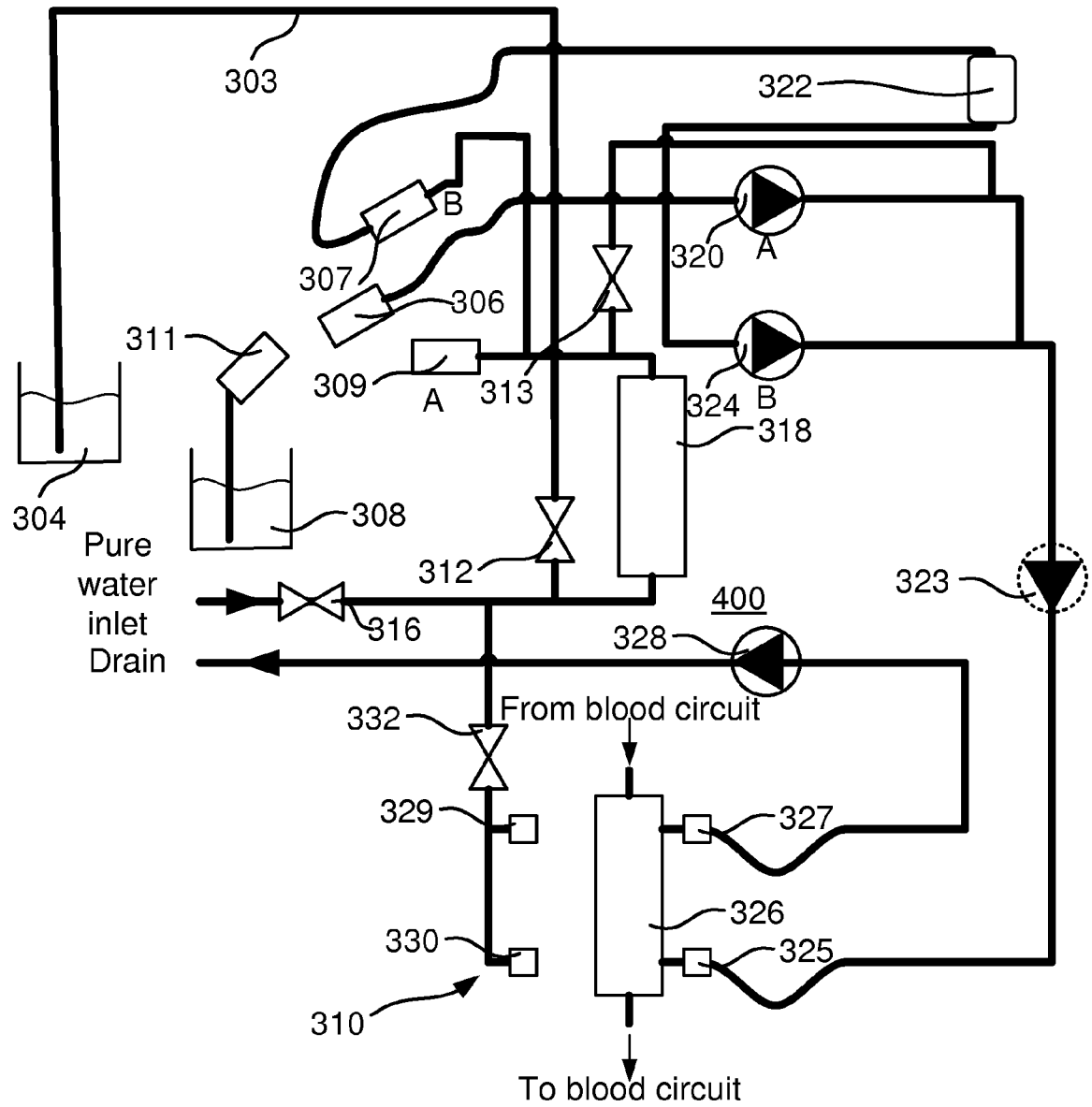

FIG. 4 illustrates a dialysis machine 400 similar to the one depicted in FIG. 3, also in respect of the position for inserting the disinfectant. The features demonstrated with reference to FIG. 3 are thus applicable also to FIG. 4, wherein the same reference numbers have been used where applicable. However, the embodiment of FIG. 4 also provides a second valve 313 which may be closed during a part of the disinfection operation, e.g. during the part of the disinfection when an amount of disinfectant is sucked from the disinfectant source 304, wherein the concentrate pump or pumps may be used to suck the disinfectant via connectors A and/or B and distribute to the fluid circuit.

Figure 5:
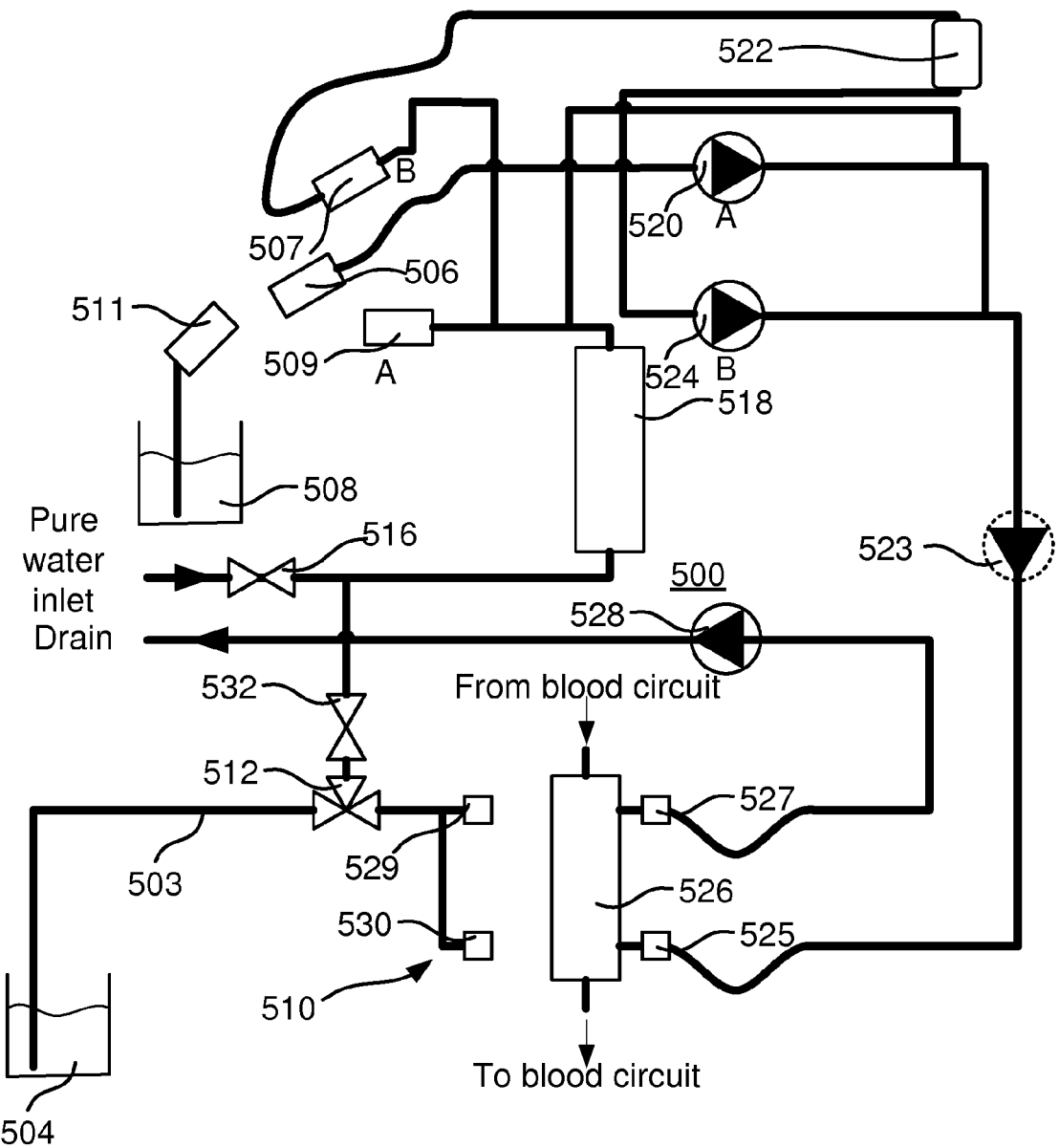

FIG. 5 illustrates a dialysis machine 500 similar to the ones depicted in FIGS. 1 and 2, but with an alternative embodiment of inserting the disinfectant. The dialysis machine 500 of FIG. 5 provides a disinfectant source 504 which is connected by a tube 503 for drawing disinfectant from a disinfectant source 504. For similar reasons as demonstrated with reference to FIG. 2, the tube 503 is connected with a first valve 512 for providing the disinfectant fluid upstream a dialyser 526 and at a position in the fluid circuit where pressure is, during treatment, such that a pressure gradient between disinfectant fluid port and fluid circuit port of the first valve 512 is provided away from the fluid circuit. The dialysis machine 500 comprises a pure water inlet which via a water valve 516 and a water heater 518 provides water for preparing desired fluids in the fluid circuit. It can also be noted that fluid connection lines, which at treatment are connected to the dialyser 526, as demonstrated above, may at disinfection be disconnected from connectors 525, 527 of the dialyser 526 and be connected to a bypass connection 510, i.e. to connectors 529, 530 of the bypass connection 510, which is employed to connect the dialysis machine upstream dialyser fluid path with the dialysis machine downstream dialyser fluid path. The bypass connection is also, via a valve 532, connected to the water line between the water valve 516 and the heater 518 to establish a connection to the pure water inlet. This enables disinfection of all parts of the fluid circuit. An advantage with the above demonstrated position for inserting the disinfectant is that it enables using the heater for heating the disinfectant for cases where the disinfectant is more efficient at higher temperatures.

The first valve 512 may comprise a three-way valve with a first connection towards the source of disinfectant 504, a second connection towards a tube in connection with the pure water inlet, i.e. via valve 532, and a third connection towards the bypass coupling 510, and the first valve 512 is arranged to either connect the first and second connections wherein disinfectant may be enabled to reach the fluid circuit, or the second and third connections for fluid flow wherein the bypass coupling may connect to the pure water inlet. The water pressure by the pure water will thus provide the pressure gradient at treatment. Furthermore, a pressure gradient is also provided towards the connectors 529, 530 being exposed only to atmospheric pressure during treatment. If the first valve 512 is malfunctioning, no disinfectant will reach the fluid circuit, and if a leak situation occurs, any fluid will leak out at the connectors 529, 530.

The output of the water heater 518 is provided to a connector A 509 and to a connector B 507, and to a position downstream a first concentrate pump A 520. The first concentrate pump A 520 is upstream connected to a connector 506 which is arranged to either be connected to the connector A 509, or to a concentrate A connector 311 providing concentrate A from a concentrate source 508.

The connector B 507 may be connected via a tube towards a dry concentrate cartridge holder 522 and the output of the dry concentrate holder is provided to a concentrate pump B 524. The concentrate pump B 524 is thus able to draw concentrate from the dry concentrate holder which is provided pure water via the connector B 507.

Concentrate output from concentrate pump A 520 is mixed with pure water downstream the concentrate pump A 520, and the mix therefrom is further downstream mixed with output from concentrate pump B 524. The mix form the dialysis fluid and is provided to a first connection 525 of a dialyser 526 wherein the fluid may be provided to the dialyzer 526 by a pump 523 and is drawn through the dialyser 526 by a flow pump 328 and exits the dialyser 526 through a second connection 527 thereof. The flow pumps 523 and 528 may be controlled such that an appropriate amount of water is removed from the patient during treatment. The dialysate, i.e. the spent dialysis fluid, is provided towards a drain by the flow pump 528.

During disinfection, the disinfection valve 512 is set in position for letting disinfectant reach the fluid circuit of the dialysis machine. Disinfectant may be drawn through the fluid circuit by the flow pump 523. Here, it is to be noted that during disinfection operation, the connector 506 may be moved to the connector A 509, whereby it can be seen that the corresponding concentrate pump A 520 can draw disinfectant through parts of the fluid circuit.

Figure 6:
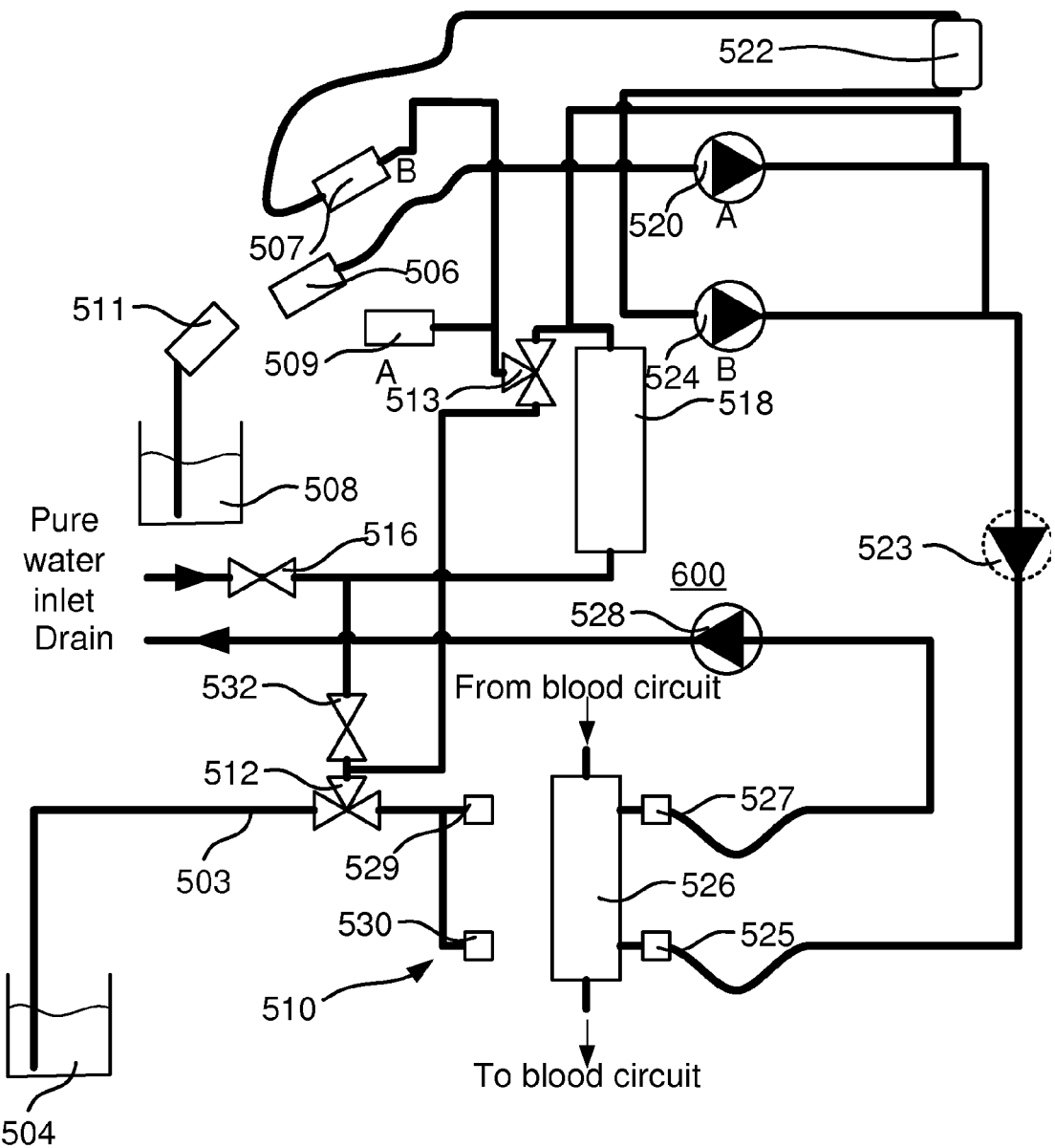

FIG. 6 illustrates a dialysis machine 600 similar to the one depicted in FIG. 5. The features demonstrated with reference to FIG. 5 are thus applicable also to FIG. 6, wherein the same reference numbers have been used where applicable. The dialysis machine 600 of FIG. 6 provides the possibility of providing disinfectant also via a further valve 513 connected to the first valve 512, wherein the concentrate pump or pumps 520, 524 may be used to suck the disinfectant via connectors A and/or B and distribute to at least respective parts of the fluid circuit. Furthermore, a pressure gradient is also provided towards the connectors 529, 530 being exposed only to atmospheric pressure during treatment. If the first valve 512 is malfunctioning, no disinfectant will reach the fluid circuit, and if a leak situation occurs, any fluid will leak out at the connectors 529, 530.

Figure 7:
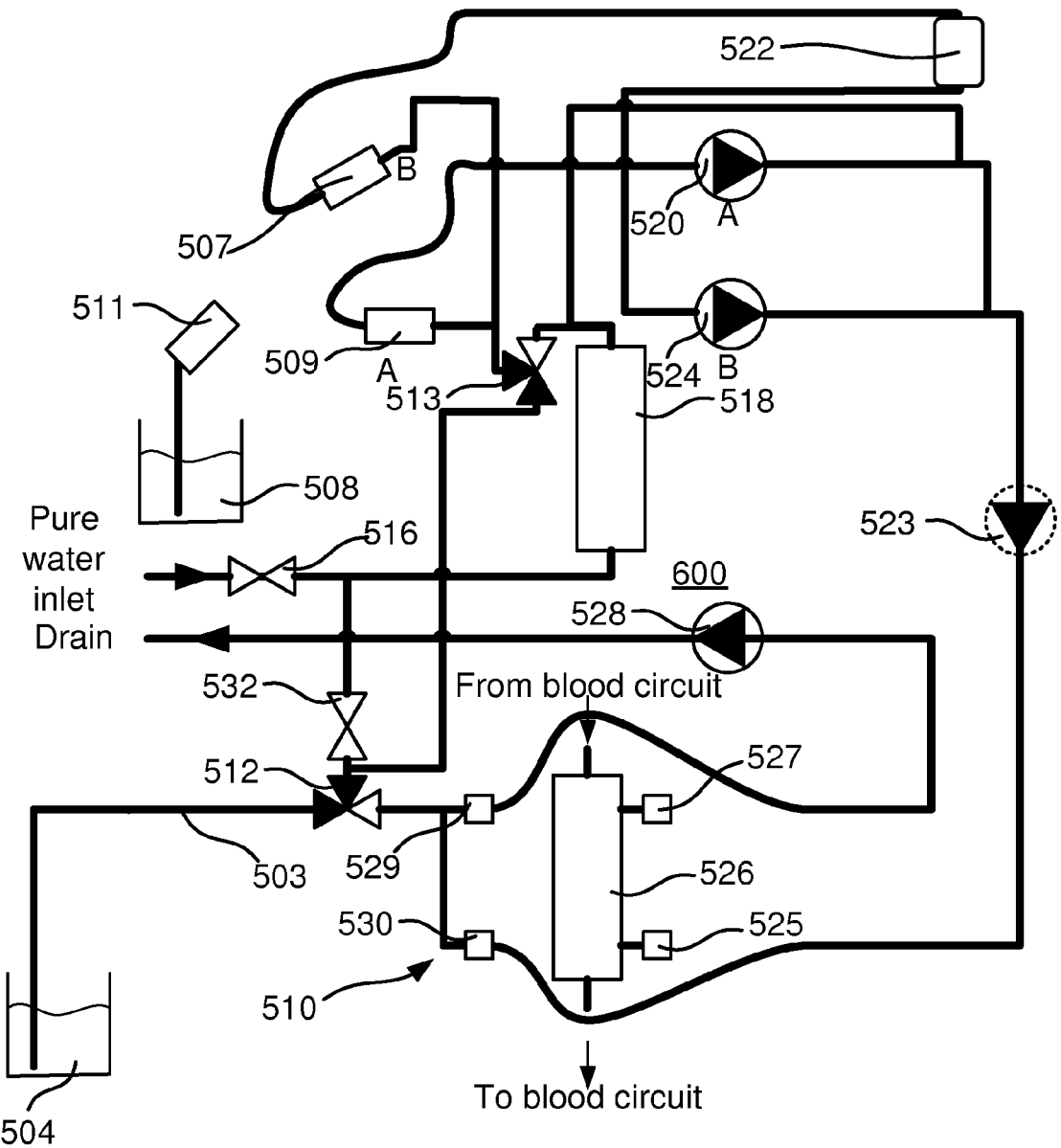

FIG. 7 illustrates the dialysis machine 600 of FIG. 6 when set up for disinfectant uptake. Here, it can be seen that the bypass coupling 510 is used wherein the fluid circuit is disconnected from connectors 525, 527 of the dialyser 526 and instead are connected to the connectors 529, 530, respectively, of the bypass coupling 510. Further, it can be seen that the disinfectant source 504 is connected via the tube 503, the first valve 512 and the further valve 513 to the connector A 509 and the connector B 507 such that for example concentrate pump A 520 and concentrate pump B 524 are enabled to suck disinfectant into the fluid circuit.

Figure 8:
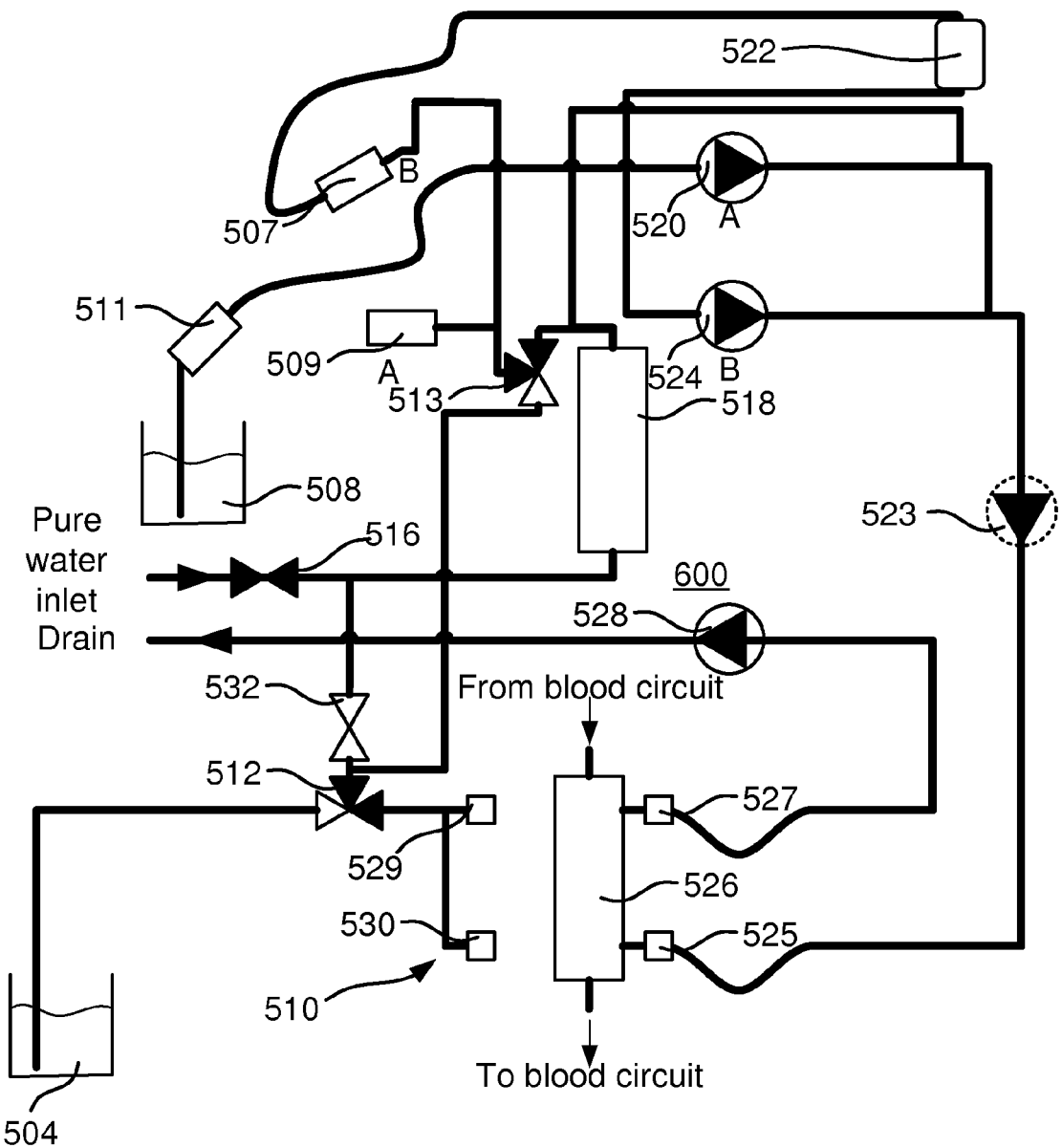

FIG. 8 illustrates the dialysis machine 600 of FIG. 6 when set up for treatment. Here, it can be seen that the dialyser 526 is connected to the fluid circuit by connectors 525, 527, the pure inlet water is enabled to provide water through water valve 516 via the heater 518, the further valve 513 and to the connector B 507 and downstream concentrate pump A 520 to enable operation as demonstrated above. The disinfectant source 504 is connected to the connectors 529, 530 via the first valve 512, wherein any disinfectant that may leak leaks through the connectors 529, 530 and not into the fluid circuit.

Figure 9:
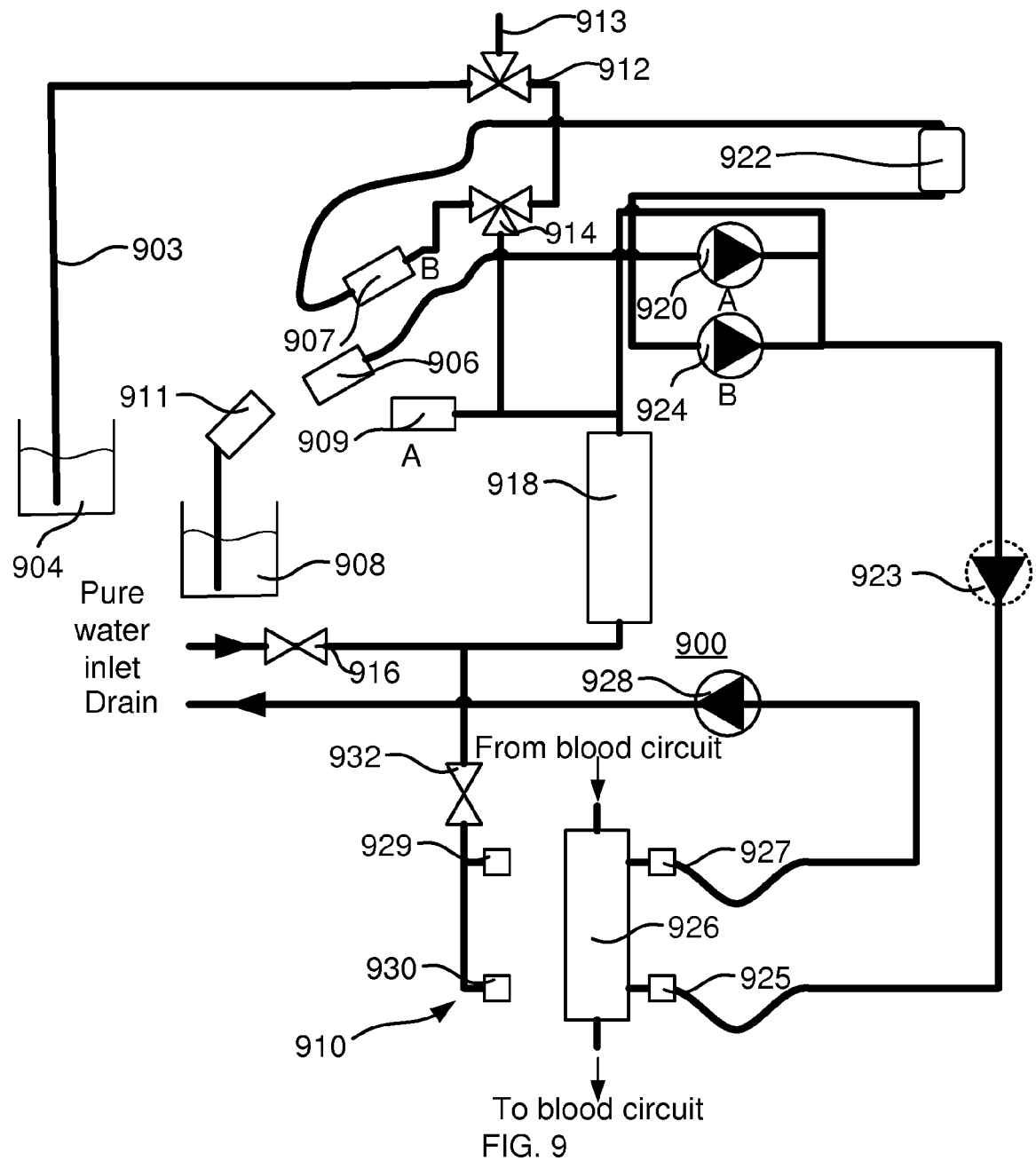

FIG. 9 illustrates a dialysis machine 900 which provides a disinfectant source 904 which is connected by a tube 903 for drawing disinfectant from a disinfectant source 904. For ensuring that the disinfectant source 904 does not provide any disinfectant to a fluid circuit of the dialysis machine 900 when a patient is connected, the tube 903 is connected with a first valve 912 for providing the disinfectant fluid for disinfecting at least a part of the fluid circuit at disinfection of the dialysis machine, wherein the tube 903 with the first valve 912 is arranged to provide the disinfectant fluid upstream a dialyser 926. The first valve 912 is a three-way valve with a first connection towards the source of disinfectant 904, a second connection towards the fluid circuit via a valve 914 with at similar function as the one 114 demonstrated with reference to FIG. 1, and a third connection 913 towards atmospheric pressure surroundings. The first valve is arranged to either connect the first and second connections for enabling disinfectant to the fluid circuit, or the first and third connections when no disinfectant should reach the fluid circuit. Thereby, a pressure gradient between disinfectant fluid port and fluid circuit port of the first valve 912 is provided away from the fluid circuit. Thus, in the latter state, the disinfectant source 904 is connected towards the third connection 913 of the first valve 912, wherein any disinfectant that may leak leaks through the third connection 913 and not into the fluid circuit. As a further note to the solution where the first valve 912 has a port towards atmospheric pressure, i.e. the surroundings, in case there is a malfunction of the first valve 912 and there happen to be a pressure below atmospheric pressure in the fluid circuit, e.g. due to any second error, the dialysis machine 900 will not suck in any disinfectant since air will be sucked from the third connection 913 because of the pressure gradient between atmospheric pressure and the pressure needed to suck the disinfectant from the disinfectant source 914. The air will be detected and/or handled by the fluid circuit by its inherent means for this. This principle is also relevant to the embodiments demonstrated above where the first valve has a connection to the bypass connectors.

The dialysis machine 900 comprises a pure water inlet which via a water valve 916 and a water heater 918 provides water for preparing desired fluids in the fluid circuit. The output of the water heater 918 is provided to a connector A 909, to a connector B 907 via the valve 914, and at a position downstream a first concentrate pump A 920. The first concentrate pump A 920 is upstream connected to a connector 906 which is arranged to either be connected to the connector A 909, or to a concentrate A connector 911 providing concentrate A from a concentrate source 908.

The connector B may be connected to a connector 907 which in turn is connected via a tube towards a dry concentrate cartridge holder 922 and the output of the dry concentrate holder is provided to a concentrate pump B 924. The concentrate pump B 924 is thus able to draw concentrate from the dry concentrate holder which is provided pure water via the connector B 907.

Concentrate output from concentrate pump A 920 is mixed with pure water downstream the concentrate pump A 920, and the mix therefrom is further downstream mixed with output from concentrate pump B 924. The mix forms the dialysis fluid and is provided to a first connection 925 of the dialyser 926 wherein the fluid may be provided to the dialyzer 926 by a pump 923 and is drawn through the dialyser 926 by a flow pump 928 and exits the dialyser 926 through a second connection 927 thereof. The flow pumps 923 and 928 may be controlled such that an appropriate amount of water is removed from the patient during treatment. The dialysate, i.e. the spent dialysis fluid, is provided towards a drain by the flow pump 928.

During disinfection, the disinfection valve 912 is set in position for letting disinfectant reach the fluid circuit of the dialysis machine. Here, it is to be noted that during disinfection operation, the connector 906 may be moved to the connector A 909, whereby it can be seen that the corresponding concentrate pump A 920 can draw disinfectant through the fluid circuit. It can also be noted that fluid connection lines, which at treatment are connected to the dialyser 926, may at disinfection be disconnected from connectors 925, 927 of the dialyser 926 and be connected to a bypass connection 910, i.e. to connectors 929, 930 of the bypass connection 910, which is employed to connect the dialysis machine upstream dialyser fluid path with the dialysis machine downstream dialyser fluid path. The bypass connection is also, via a valve 932, connected to a water line between the water valve 916 and the heater 918 to establish a connection to the pure water inlet. This enables disinfection of all parts of the fluid circuit.

Figure 14:
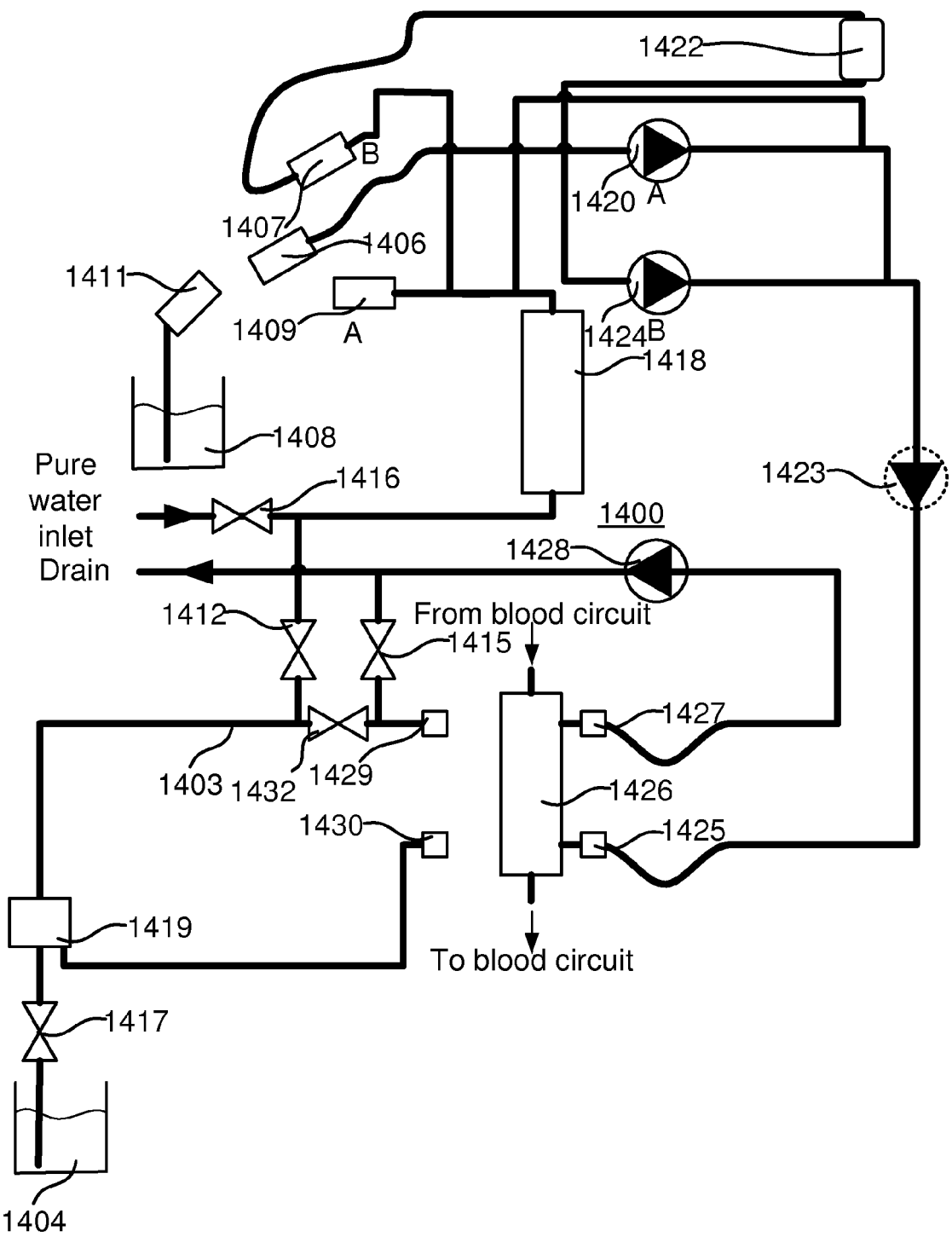
FIGS. 14 and 15 schematically illustrate a dialysis machine with an arrangement for disinfection according to an embodiment.
Figure 15:
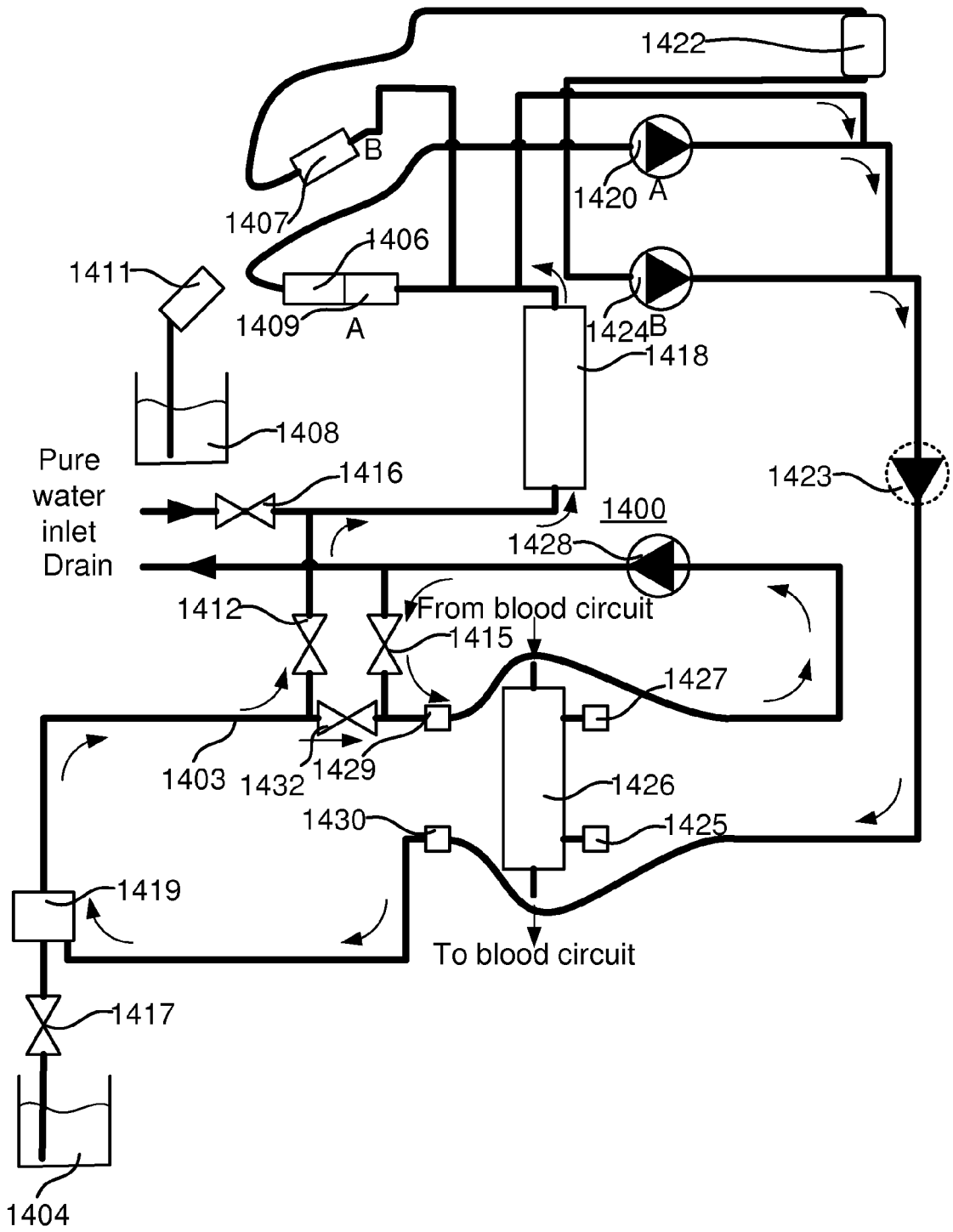

FIGS. 14 and 15 schematically illustrate a dialysis machine 1400 with an arrangement for disinfectant according to an embodiment. FIG. 14 illustrates the machine 1400 arranged for treatment, and FIG. 15 illustrates the machine 1400 arranged for disinfection. The dialysis machine 1400 provides a disinfectant source 1404 which is connected by a tube 1403 for drawing disinfectant from the disinfectant source 1404. A disinfection tank 1419 is provided for loading the machine 1400 with disinfectant for the next disinfection procedure. This is performed by opening a valve 1417, preferably at the end of one disinfection session, and filling-up the disinfectant tank 1419 from the disinfectant source.

For similar reasons as demonstrated with reference to FIG. 5, the tube 1403 is connected with a first valve 1412 for providing the disinfectant fluid upstream a dialyser 1426 and at a position in the fluid circuit where pressure is, during treatment, such that a pressure gradient between disinfectant fluid port and fluid circuit port of the first valve 1412 is provided away from the fluid circuit. It is to be noted that during treatment, the dialysis machine 1400 comprises a pure water inlet which via a water valve 1416 and a water heater 1418 provides water for preparing desired fluids in the fluid circuit. It can also be noted that fluid connection lines, which at treatment are connected to the dialyser 1426, as demonstrated above, may at disinfection be disconnected from connectors 1425, 1427 of the dialyser 1426 and be connected to the connectors 1429 and 1430, among which the connector 1430 is employed to connect the dialysis machine upstream dialyser fluid path with the disinfection fluid tank 1419 to establish a connection to the pure water inlet path, and the connector 1429 is employed to connect the dialysis machine downstream dialyser fluid path to a drain line of the dialysis machine via a fourth valve 1415. Thus, a first path and a second path are formed at disinfection, where the first path comprises the parts upstream the dialyser at treatment, which may be considered as the "clean side" of the machine since no spent dialysate should be present there, and the second path comprises the parts downstream the dialyser at treatment.

The first path thus comprises a loop of the disinfection fluid tank 1419 via the first valve 1412 and a path from the pure water inlet line to the dialyser upstream connector 1430 to the disinfection fluid tank 1419 again. This enables disinfection of all parts of the fluid circuit upstream the dialyser. The second path comprises a loop of the dialyser downstream connector 1429 and a drainage pump 1428 via the fourth valve 1415 to the dialyser downstream connector 1429 again. The disinfectant may be provided to the loop of the second path through a bypass valve, e.g. one normally present in dialysis apparatuses prior to the dialyser 1426 and normally having the function to short-circuit the flow to pass the dialyser 1426 towards the drain in case the dialysate is found, e.g. by measurements, to be unsuitable to be sent to the dialyser 1426. That bypass valve may in the above demonstrated structure be used to provide disinfectant from the first path to the second path. Alternatively, the disinfectant is provided through a fifth valve 1432, as illustrated as an option in FIGS. 14 and 15. The fifth valve 1432 may be controlled together with the fourth valve 1415 such that the drainage pump 1428 is enabled to suck up the disinfectant. The fifth valve 1432 may alternatively be a one-way valve. However, other bypass valve arrangements for providing the disinfectant to that loop are equally feasible, such as a one-way valve between the tube at the connector 1430 and the tube at connector 1429, a branch of the tube 1403 connected to the loop of the second path with a valve arrangement to the second path, for example to the input of the drainage pump 1428, etc. This enables disinfection of all parts of the fluid circuit downstream the dialyser. When not performing disinfection, the first and fourth valves 1412, 1415 are closed. The fifth valve 1432 in the option given above may be open during treatment such that any leakage is provided to the connector 1429.

This enables disinfection of all parts of the fluid circuit both upstream and downstream the dialyser.

The water pressure by the pure water will thus provide the pressure gradient at treatment. Furthermore, a pressure gradient is also provided towards the connector 1430 being exposed only to atmospheric pressure during treatment. If the first valve 1412 is malfunctioning, no disinfectant will reach the fluid circuit, and if a leak situation occurs, any fluid will leak into the disinfectant tank 1419 and out at the connector 1430.

The output of the water heater 1418 is provided to a connector A 1409 and to a connector B 1407, and to a position downstream a first concentrate pump A 1420. The first concentrate pump A 1420 is upstream connected to a connector 1406 which is arranged to either be connected to the connector A 1409, or to a concentrate A connector 1411 providing concentrate A from a concentrate source 1408.

The connector B 1407 may be connected via a tube towards a dry concentrate cartridge holder 1422 and the output of the dry concentrate holder is provided to a concentrate pump B 1424. The concentrate pump B 1424 is thus able to draw concentrate from the dry concentrate holder which is provided pure water via the connector B 1407.

Concentrate output from concentrate pump A 1420 is mixed with pure water downstream the concentrate pump A 1420, and the mix therefrom is further downstream mixed with output from concentrate pump B 1424. The mix forms the dialysis fluid and is provided to a first connection 1425 of a dialyser 1426 wherein the fluid may be pumped through the dialyser 1426 by a flow pump 1423 and/or drawn through the dialyser 1426 by a flow pump 1428 and exits the dialyser 1426 through a second connection 1427 thereof. The flow pumps 1423 and 1428 may be controlled such that an appropriate amount of water is removed from the patient during treatment. The dialysate, i.e. the spent dialysis fluid, is provided towards a drain by the flow pump 1428.

During disinfection, the disinfection valve 1412 is set in position for letting disinfectant reach the fluid circuit of the dialysis machine. Here, it is to be noted that during disinfection operation, the connector 1406 may be moved to the connector A 1409, whereby it can be seen that the corresponding concentrate pump A 1420 can draw disinfectant through parts of the fluid circuit, i.e. the branch of pump A 1420. Similar applies for pump B 1424 and the branch of pump B 1424. This enables disinfection of all parts of the fluid circuit.

Figure 10:
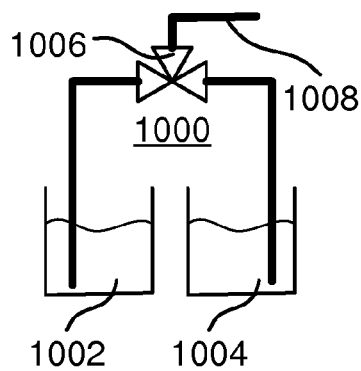
FIG. 10 schematically illustrates a disinfectant source according to an embodiment.

FIG. 10 illustrates a disinfectant source 1000 according to an embodiment. In the embodiments of dialysis apparatuses above, a single source of disinfectant has been illustrated. This single source of disinfectant may be substituted by a multiple source of disinfectant, e.g. as demonstrated with reference to FIG. 10. The disinfectant source comprises a first source of disinfectant 1002 and a second source of disinfectant 1004. Each of the sources of disinfectant 1002, 1004 is connected to a port of a disinfectant selection valve 1006, respectively, wherein the valve is arranged to select the port to draw disinfectant from to provide to an output 1008 of the disinfectant source 1000. Embodiments with three or more sources of disinfectants are also possible.

Figure 12:
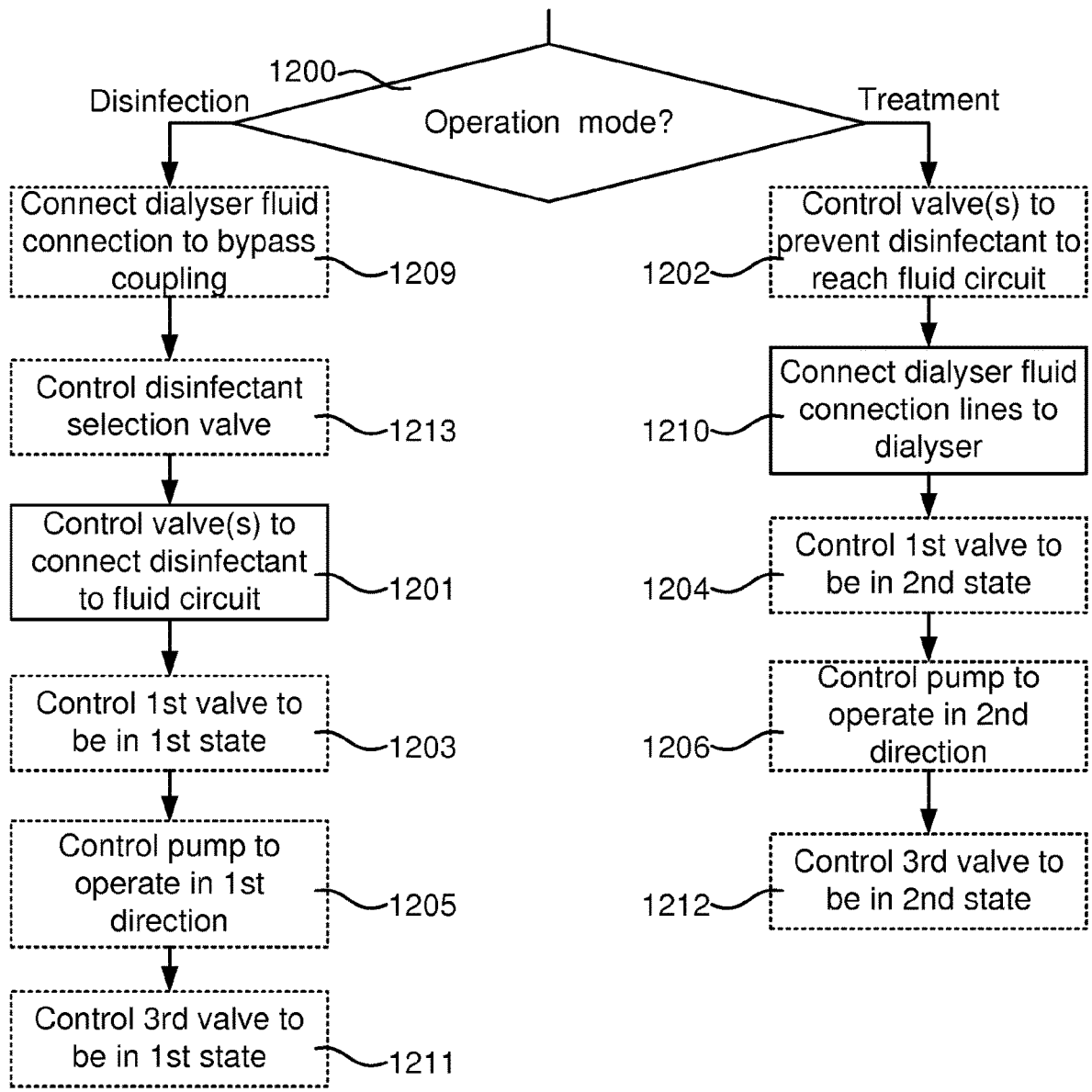
FIG. 12 is a flow chart schematically illustrating methods according to embodiments.

FIG. 12 is a flow chart schematically illustrating methods according to embodiments. The methods relate to controlling a fluid circuit for providing a dialysis fluid to a dialyser and disinfection operation of a dialysis machine according to what is demonstrated above with reference to any of FIGS. 2 to 9, 14 and 15, and also their application with a disinfectant source as demonstrated with reference to FIG. 10. It is determined in 1200 whether the dialysis machine is to operate in disinfection operation mode or in treatment operation mode. The method comprises controlling 1202 the first valve to prevent connection of the disinfectant source to the fluid circuit during treatment; and controlling 1201 the first valve to connect the disinfectant source to the fluid circuit during disinfection operation.

According to an embodiment the method comprises controlling 1203 the first valve to be in the first state and controlling 1205 the pump for concentrate distribution to provide fluid flow in a first direction during disinfection operation. For treatment operation, the method comprises controlling 1204 the first valve to be in the second state and controlling 1206 the pump for concentrate distribution to provide fluid flow in a second direction opposite to the first direction during treatment. This is for example applicable where the position is downstream a pump for concentrate distribution and the first valve is a three-way valve with a first connection towards the source of disinfectant, a second connection towards the pump for concentrate distribution, and a third connection towards the fluid circuit leading to the dialyser, and the first valve may be arranged to either connect the first and second connections in a first state, or the second and third connections for fluid flow in a second state.

For an embodiment where the fluid circuit comprises a bypass coupling as a receiving part for the dialyser connection lines of the dialysis machine as demonstrated above, the method may have an embodiment that comprises, at treatment, connecting 1210 the dialyser with the dialysis machine upstream dialyser fluid path and the dialysis machine downstream dialyser fluid path, respectively, and controlling 1202 the valve to connect the second and third connections for fluid flow; and at disinfection operation, connecting 1209 to the bypass coupling, i.e. the dialysis machine upstream dialyser fluid path and the dialysis machine downstream dialyser fluid path, to bypass the dialyser, and controlling 1201 the valve to connect the first and third connections for fluid flow. The fluid circuit may further comprise a third valve being a three-way valve with a first connection towards the second connection of the first valve, a second connection towards a tube in connection with the pure water inlet, and a third connection towards a concentrate connector of the machine. In such an embodiment, the method may comprise, at treatment, controlling 1212 the third valve to connect the second and third connections for fluid flow; and, at disinfection operation, controlling 1211 the third valve to connect the first and third connections for fluid flow.

A disinfectant selection valve may be arranged to enable selection of one of several disinfectants as the source of disinfectant. This can be done for the entire disinfection process, or a more complex sequence or scheme of disinfection operations with use of more than one disinfectant, e.g. in sequence, can be employed. The method may thus comprise controlling 1213 the disinfectant selection valve at disinfection operation according to a predetermined disinfection scheme.

Figure 13:
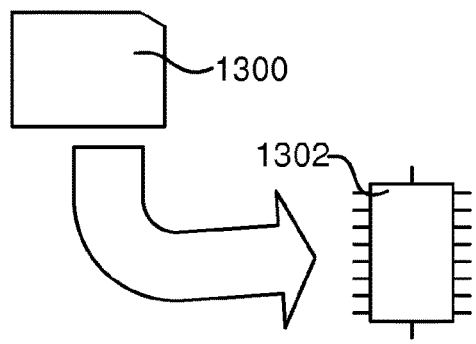
FIG. 13 schematically illustrates a computer-readable medium and a processor on which a computer program held by the computer-readable medium can be executed.

The methods according to the present invention are suitable for implementation with aid of processing means, such as computers and/or processors, especially for the case where the dialysis machine is computer controlled. Therefore, there is provided computer programs, comprising instructions arranged to cause the processing means, processor, or computer to perform the steps of any of the methods according to any of the embodiments described with reference to FIG. 12. The computer programs preferably comprises program code which is stored on a computer readable medium 1300, as illustrated in FIG. 13, which can be loaded and executed by a processing means, processor, or computer 1302 to cause it to perform the methods, respectively, according to embodiments of the present invention, preferably as any of the embodiments described with reference to FIG. 12. The computer 1302 and computer program product 1300 can be arranged to execute the program code sequentially where actions of any of the methods are performed stepwise. The processing means, processor, or computer 1302 is preferably what normally is referred to as an embedded system. Thus, the depicted computer readable medium 1300 and computer 1302 in FIG. 13 should be construed to be for illustrative purposes only to provide understanding of the principle, and not to be construed as any direct illustration of the elements.

The invention has mainly been described above with reference to a few embodiments. However, as is readily appreciated by a person skilled in the art, other embodiments than the ones disclosed above are equally possible within the scope of the invention, as defined by the appended patent claims.

The invention claimed is:

1. A dialysis machine comprising:
a dialyser;
a fluid line in fluid communication with the dialyser;
an inlet valve configured to enable fluid to flow into the fluid line towards the dialyser during a dialysis treatment;
a disinfectant line connected to the fluid line via a disinfectant valve upstream of the dialyser, the disinfectant valve enabling a disinfectant fluid to be provided to at least part of the fluid line during a disinfection procedure; and
a controller programmed to open the inlet valve, while the disinfectant line is connected to a source of disinfectant fluid, to create a positive pressure gradient across the disinfectant valve as fluid flows into the fluid line towards the dialyser, the positive pressure gradient ensuring that the disinfectant fluid from the source of disinfectant fluid does not leak into the fluid line during the dialysis treatment.

2. The dialysis machine of claim 1, wherein the fluid is water.

3. The dialysis machine of claim 2, wherein the controller is programmed to cause the water to mix with concentrate to create dialysis fluid after the water passes a position of the disinfectant valve along the fluid line.

4. The dialysis machine of claim 2, wherein the disinfectant valve is connected to the fluid line downstream of a pump configured to pump concentrate to be mixed with the water to create dialysis fluid.

5. The dialysis machine of claim 1, wherein the fluid is dialysis fluid.

6. The dialysis machine of claim 1, which includes a pump configured to pump dialysis fluid through the fluid line towards the dialyser during the dialysis treatment, wherein the controller is programmed to use the pump to pump disinfectant fluid from the source of disinfectant fluid through the fluid line during the disinfection procedure.

7. The dialysis machine of claim 6, wherein the disinfectant valve is connected to the fluid line upstream of the pump.

8. A dialysis machine comprising:
a dialyser;
a fluid line in fluid communication with the dialyser;
a pump configured to cause an amount of water to be removed from the patient during a dialysis treatment;
an inlet valve configured to enable fluid to flow into the fluid line towards the dialyser during the dialysis treatment;
a disinfectant line connected to the fluid line via a disinfectant valve upstream of the pump, the disinfectant valve enabling a disinfectant fluid to be provided to at least part of the fluid line during a disinfection procedure; and
a controller programmed to open the inlet valve, while the disinfectant line is connected to a source of disinfectant fluid, to create a positive pressure gradient across the disinfectant valve as fluid flows into the fluid line towards the dialyser, the positive pressure gradient ensuring that the disinfectant fluid from the source of disinfectant fluid does not leak into the fluid line during the dialysis treatment.

9. The dialysis machine of claim 8, wherein the pump is positioned upstream of the dialyser.

10. The dialysis machine of claim 8, wherein the pump is positioned downstream of the dialyser.

11. The dialysis machine of claim 8, wherein the pump is configured to pump fresh dialysis fluid towards the dialyser during the dialysis treatment.

12. The dialysis machine of claim 8, wherein the pump is configured to pump spent dialysis fluid from the dialyser during the dialysis treatment.

13. The dialysis machine of claim 8, wherein the controller is programmed to use the pump to pump disinfectant fluid from the source of disinfectant fluid through the fluid line during the disinfection procedure.

14. A method of controlling a dialysis machine including a dialyser, a fluid line in fluid communication with the dialyser, an inlet valve configured to enable fluid to flow into the fluid line towards the dialyser during a dialysis treatment, a disinfectant line connected to the fluid line via a disinfectant valve upstream of the dialyser, the disinfectant valve enabling a disinfectant fluid to be provided to at least part of the fluid line during a disinfection procedure, and a controller programmed to open the inlet valve, while the disinfectant line is connected to a source of disinfectant fluid, to create a positive pressure gradient across the disinfectant valve as fluid flows into the fluid line towards the dialyser, the positive pressure gradient ensuring that the disinfectant fluid from the source of disinfectant fluid does not leak into the fluid line during the dialysis treatment, the method comprising:

connecting the disinfectant line to the fluid line via the disinfectant valve upstream of the dialyser, the disinfectant valve enabling the disinfectant fluid to be provided to at least part of the fluid line during the disinfection procedure, the fluid line enabling fluid to flow towards the dialyser during the dialysis treatment; and opening the inlet valve to the fluid line, while the disinfectant line is connected to the source of disinfectant fluid, to create the positive pressure gradient across the disinfectant valve as fluid flows into the fluid line towards the dialyser, the positive pressure gradient ensuring that the disinfectant fluid from the source of disinfectant fluid does not leak into the fluid line during the dialysis treatment.

15. The method of claim 14, wherein the fluid is water.

16. The method of claim 15, which includes causing the water to mix with concentrate to create dialysis fluid after the water passes a position of the disinfectant valve along the fluid line.

17. The method of claim 15, which includes connecting the disinfectant valve to the fluid line downstream of a pump configured to pump concentrate to be mixed with the water to create dialysis fluid.

18. The method of claim 14, wherein the fluid is dialysis fluid.

19. The method of claim 14, which includes operating a pump to pump dialysis fluid through the fluid line towards the dialyser during the dialysis treatment, and which includes operating the pump to pump disinfectant fluid from the source of disinfectant fluid through the fluid line during the disinfection procedure.

20. The method of claim 19, which includes connecting the disinfectant valve to the fluid line upstream of the pump.

21. The method of claim 14, which includes opening a tank valve, which connects the source of disinfectant fluid to a disinfection tank, to fill the disinfection tank from the source of disinfectant fluid, thereby loading the disinfection tank for a next disinfection procedure.

22. The method of claim 21, wherein opening the tank valve to fill the disinfection tank from the source of disinfectant fluid is performed at the end of one disinfection procedure.

23. The method of claim 21, further comprising:
fluidly connecting the disinfection tank upstream of the dialyser to establish a fluid connection between the disinfection tank and a pure water inlet; and
fluidly connecting a drain line downstream of the dialyser.

* * * * *